United States Patent [19]

Gauderer et al.

[11] Patent Number: 4,863,438
[45] Date of Patent: Sep. 5, 1989

[54] LOW PROFILE GASTROSTOMY DEVICE

[75] Inventors: Michael L. Gauderer, Cleveland; George J. Picha, Independence; Dennis Siedlak, Willoughby Hills, all of Ohio

[73] Assignee: Applied Medical Technology, Inc., Independence, Ohio

[21] Appl. No.: 803,386

[22] Filed: Nov. 29, 1985

[51] Int. Cl.$^4$ .................................... A61M 5/005
[52] U.S. Cl. .................... 604/247; 604/105; 604/175; 604/256
[58] Field of Search ............... 604/93, 117, 101, 279, 604/104, 175, 297, 105, 96, 178, 271, 280, 247, 256

[56] References Cited

U.S. PATENT DOCUMENTS

| | | | |
|---|---|---|---|
| 2,087,511 | 7/1937 | Gould | 604/279 |
| 2,230,226 | 2/1941 | Auzin | 604/104 |
| 2,649,092 | 8/1953 | Wallace | 604/105 |
| 3,253,594 | 5/1966 | Matthews et al. | 604/96 |
| 3,333,588 | 8/1967 | Schulte | 604/175 |
| 3,812,841 | 5/1974 | Isaacson | 604/101 |
| 3,915,171 | 10/1975 | Shermeta | 604/101 |
| 4,315,513 | 2/1982 | Nawash et al. | 604/283 |
| 4,416,273 | 11/1983 | Grimes | 604/283 |

Primary Examiner—C. Fred Rosenbaum
Assistant Examiner—Kathleen A. Daley
Attorney, Agent, or Firm—Renner, Otto, Boisselle & Sklar

[57] ABSTRACT

Device includes a flexible, hollow tube portion having a resiliently deformable mushroom shape tip at the inner end thereof to retain the tube in the stomach or other viscera of a patient and provide an enlarged internal chamber for the mounting of a one-way flapper valve therein and the seating of the flapper valve against the inner end of the tube portion to prevent reflux of gastric contents while permitting the influx of fluids into the stomach or other viscera of the patient through the tube portion. A pair of oppositely extending, relatively short, flat wings are integrally molded on the outer end of the tube portion to make the tube portion self-retaining and flush up against the skin. The wings are relatively narrow in width, whereby the tube portion may be rotated a part turn to bring the wings into contact with different areas of the skin if irritation should occur. A plug is integrally molded on the outer end of one of the wings by a flexible membrane which permits the plug to be inserted into the tube at the outer end thereof and removed therefrom as desired.

24 Claims, 1 Drawing Sheet

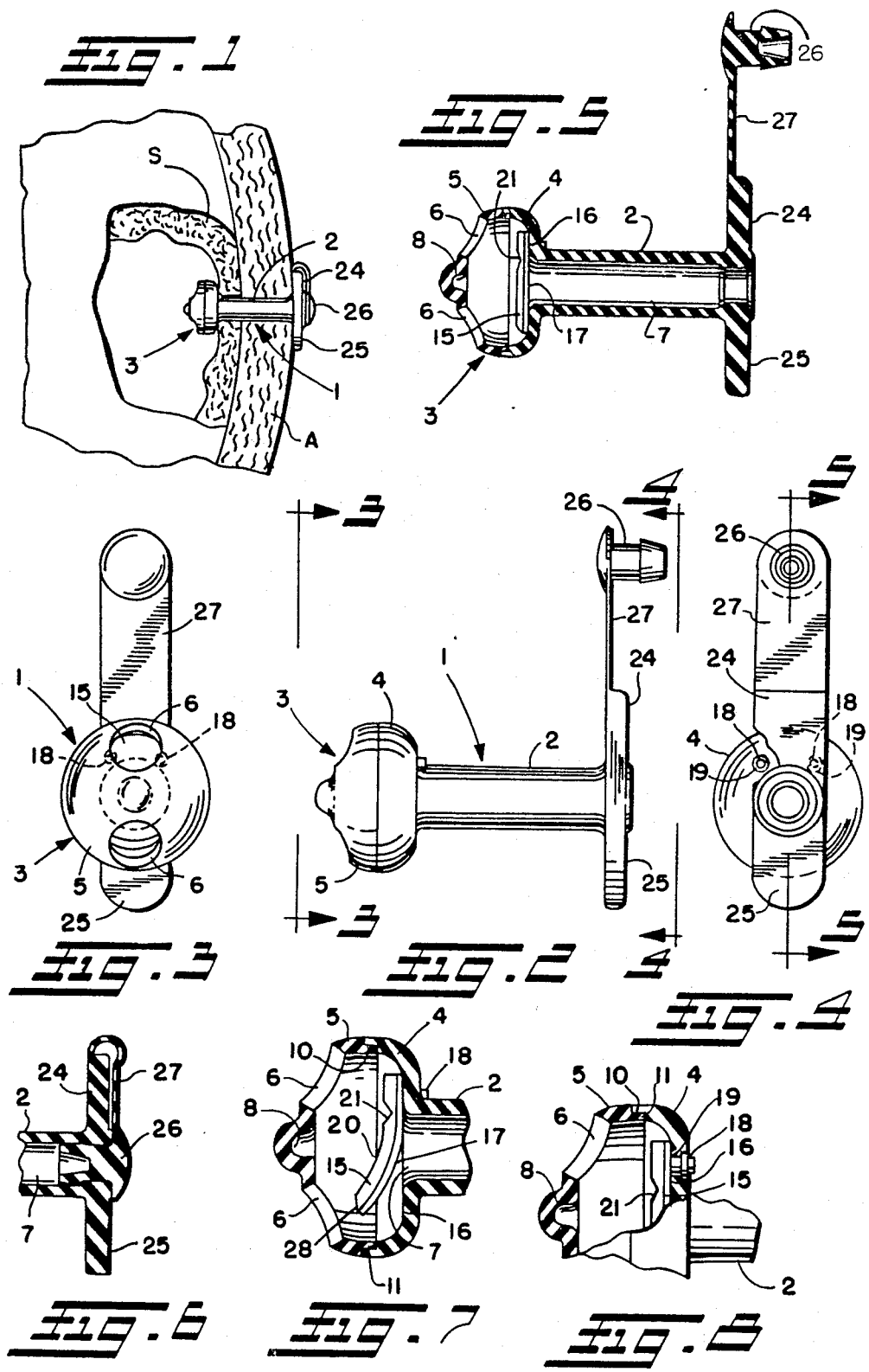

LOW PROFILE GASTROSTOMY DEVICE

BACKGROUND OF THE INVENTION

This invention relates generally as indicated to a low profile gastrostomy device which is especially designed to be inserted through an opening in the wall of the abdomen and stomach of a patient for use in supply nutrients and other fluids including medication into the stomach. Also, such a device can be used for decompression, and provides access for examination endoscopically, for example, using fiber optics. Other uses requiring insertion of a tube into other viscera of the body may be made of the device, such as urinary bladder drainage, ileostomy, jejunostomy, and cystostomy.

Certain medical conditions require the long term access for such purposes as internal feedings and/or medication to a person's stomach or other viscera of the body. This may be accomplished by inseting a tube through a surgical opening into the stomach or other viscera.

Problems with conventional gastrostomy tubes are common in both adults and children. These range from stomal irritation to more serious mishaps. Accidental removal and internal migration are also oftentimes encountered with conventional gastrostomy tubes.

To eliminate these problems, the low profile gastrostomy device of the present invention was developed which is simple in design and use, is substantially flush with the skin, and is self-retaining and non-refluxing. Such device is also biocompatible, long lasting, and can be used in an established gastrostomy.

One type of skin level feeding gastrostomy tube is disclosed in U.S. Pat. No. 4,315,513. The device shown in such patent includes a malecot tip on the inner end of the tube for retaining the tube in the stomach and an exterior assembly which rests substantially flush against the outside abdominal wall. A skin protector disk is disposed between an outer flange on the external assembly and the exterior of the abdominal wall to space the external assembly a slight distance from the abdominal wall so as to allow air to reach the underlying skin. Also, a one-way valve is mounted within the exterior assembly to prevent the back flow of fluids or gas from the stomach without having to clamp a tube extension. A cap may be used to close off the outer end of the tube when not in use.

Also, U.S. Pat. No. 3,915,171 shows another gastrostomy tube including a first retention bulb at the inner end of the tube which is disposed in bearing engagement against the inside stomach wall and a second inflatable retention bulb spaced from the first retention bulb to engage the outer abdominal wall when inflated. A plug is removable from the outer end of the tube to open the tube as desired. The plug is connected to the tube by a flexible strap to prevent the plug from being separated from the tube.

These devices have the drawback that they are relatively large and rigid, may be made of natural rubber, and are complicated and expensive to make. Also, the exterior retention devices are potentially irritating to the skin, and are not as flush with the skin as one would like. Some devices also require the use of a retention balloon and an access port for inflation and deflation.

SUMMARY OF THE INVENTION

With the foregoing in mind, it is a principal object of this invention to provide a relativel simple, skin level, non-refluxing gastrostomy device and the like for long term internal feedings and the like.

Another object is to provide such a device with a novel one-way valve arrangement for permitting flow in one direction only into the stomach through the device.

Still another object is to provide such a device with novel retention means for retaining the inner end of the device within the stomach and the outer end of the device flush up against the skin.

A further object is to provide such a device which is made entirely of a non-rigid plastic material that is compatible with human tissue.

Another object is to make such a device of a three piece molded construction which is permanently assembled prior to use.

In accordance with one aspect of the invention, the device includes a flexible, hollow tube portion having a resiliently deformable mushroom shape tip at the inner end thereof providing an enlarged internal chamber for the mounting of a one-way flapper valve therein and the seating of the flapper valve againt the inner end of the tube portion to prevent reflux of gastric contents while permitting the influx of fluids therethrough.

In accordance with another aspect of the invention, the mushroom shape tip includes an inner semi-spherical portion which is integrally molded on the inner end of the tube and a separate outer cap portion that is secured in place after the flapper valve member has been mounted within the interior of the inner semi-spherical portion.

In accordance with yet another aspect of the invention, a pair of oppositely extending relatively short, flat wings are integrally molded on the outer end of the tube to make the tube self-retaining and flush up against the skin. The wings are relatively narrow in width, whereby the tube may be rotated part of a turn to bring the wings into contact with different areas of the skin if irritation should occur.

Also in accordance with the invention, a plug is desirably integrally moled on the outer end of one of the wings by a flexible membrane which permits the plug to be inserted into the opening in the outer end of the tube to completely close off such opening and removed therefrom as desired.

To the accomplishment of the foregoing and related ends, the invention, then, comprises the features hereinafter fully described and particularly pointed out in the claims, the following description and the annexed drawings setting forth in detail a certain preferred embodiments of the invention, this being indicative, however, of but one of the various ways in which the principles of the invention may be employed.

BRIEF DESCRIPTION OF THE DRAWINGS

In the annexed drawings:

FIG. 1 is a side elevation view of a preferred form of low profile gastrostomy device in accordance with this invention shown inserted through an opening through the abdominal wall and stomach of a patient, such device having a plug inserted in the outer end of the tube of the device;

FIG. 2 is an enlarged side elevation view of the device of FIG. 1 showing the plug removed from the outer end of the tube;

FIG. 3 is an end elevation view of the device of FIG. 2 as seen from the left end thereof;

FIG. 4 is an end elevation view of the device of FIG. 2 as seen from the right end thereof;

FIG. 5 is a longitudinal section through the device of FIG. 4 taken along the plane of the line 5—5 thereof, showing the flapper valve of the device in the closed position and the plug removed from the outer end of the tube;

FIG. 6 is a fragmentary longitudinal section through the right or outer end of the device showing the plug inserted in the outer end of the tube;

FIG. 7 is an enlarged fragmentary longitudinal section through the enlarged tip at the left or inner end of the device showing the flapper valve in the open position; and FIG. 8 is an enlarged fragmentary section through the enlarged tip at the inner end of the device showing the manner of attachment of the flapper valve internally within the enlarged tip.

DETAILED DESCRIPTION OF THE PREFERRED EMBODIMENT

Referring now in detail to the drawings, a preferred form of low profile gastrostomy feeding device in accordance with this invention is generally indicated by the reference numeral 1. Preferably, such device consists of three separately molded parts, each connected together as described hereafter. The main part comprises a flexible hollow tube 2 preferably of a length just long enough to extend through an opening in the abdominal wall A and stomach wall S of a patient as schematically illustrated in FIG. 1. A longitudinal passage 7 extends the entire length of the tube from one end to the other.

At the inner end of the tube 2 is an enlarged resiliently deformable mushroom shaped tip 3 formed as by integrally molding an enlarged semi-spherical end portion 4 on the inner end of the tube and attaching a separately molded or outer cap portion 5 to the axial outer end of the semi-spherical end portion utilizing a suitable adhesive. The outer cap portion 5 is generally dome shape and has a pair of laterally spaced diametrically aligned holes 6 therein to provide for the flow of fluid through the tube and into the stomach.

At the axial center of the outer cap portion 5 is a center recess 8 (see FIGS. 5, 7 and 8) which may be engaged by a mandril-like tool inserted through the tube from the outer end thereof to facilitate implacement of the device in a patient's body through a surgical opening such as an established gastrostomy, constructed by laparotomy or the percutaneous endoscopic technique. Forward presure on the mandril distends the mushroom tip 3 to facilitate insertion through the surgical opening. When the enlarged tip is inside the stomach, the mandril is removed, whereby the resiliency of the mushroom shaped tip 3 causes the tip to bulge outward as shown in the drawings in order to retain the tip's shape within the stomach.

For ease of attachment of the outer cap portion 5 to the semi-spherical portion 4 of the enlarged tip 3, the axial outer end of the semi-spherical portion desirably has a counterbore 10 therein for receipt of a stepped shoulder 11 on the inner end of the cap portion as shown in FIGS. 7 and 8. This provides a substantial interface between the two surfaces which are bonded together using a suitable adhesive. Before making such attachment, a one-way flapper valve 15 is desirably attached to a relatively flat, radially extending internal end wall 16 of the semi-spherical end portion 4 surrounding the axial inner end of the hollow tube 2.

As clearly shown in FIGS. 5, 7 and 8, the side 17 of the flapper valve 15 facing the end wall 16 is substantially flat for flat sealing engagement with such end wall to prevent reflux of gastric contents through such tube while permitting the influx of fluids therethrough. A pair of flanged mounting projections or studs 18 may be integrally molded on the back side 17 of the flapper valve adjacent one end thereof to facilitate attachment of the flapper valve to such end wall by inserting such projections into similarly shaped openings 19 in the end wall 16 which are located radially outwardly of the O.D. of the tube 2 (see FIGS. 3, 5 and 8). Also, a suitable adhesive may be applied to the contacting surfaces of the flapper valve and inner wall 16 in the region of the projections 18 to assist in maintaining the parts in the desired assembled relation.

The opposite side 20 of the flapper valve 15 is also desirably substantially flat but may be provided with a generally V-shaped groove 21 extending across substantially the full width of the flapper valve radially inwardly of the projections 18 and substantially tangent to the adjacent edge of the longitudinal passage 7 through the tube to provide a bend line or hinge line adjacent the inner end of such passage to permit the valve to freely flex along the bend line for opening and closing such passage. However, it should be understood that the flapper valve will function quite well without the groove.

Integrally molded on the axial outer end of the tube 2 are a pair of diametrically oppositely extending, relatively short, substantially flat wings 24, 25 which, along with the mushroom shaped tip, make the device self-retaining in the patient when the mushroom shaped tip 3 has expanded against the inside wall of the stomach S and the wings are generally flush with the outside abdominal wall A as shown in FIG. 1. The wings 24, 25 are preferably relatively narrow in width, whereby if irritation of the skin should occur in the area of the wings, the tube can readily be rotated a part turn so that the wings overlie different non-irritated areas of the skin.

Also, a plug 26 is desirably integrally connected to the outer end of one of the wings 24 by means of a flexible membrane 27 which permits the plug to be inserted into the axial outer end of the passage 7 in the tube 2 to completely close off such passage and removed therefrom as desired without fear of losing or misplacing the plug.

The entire device, including the tube 2 with integrally molded semi-spherical portion 4 at the axial inner end thereof and the wings 24, 25 and plug 26 at the axial outer end and associated cover 5 and flapper valve 15 are all desirably made of a biocompatible long-lasting resiliently deformable material such as medical grade silicone rubber. Moreover, although the dimensions of the device may vary somewhat, it has been found that three different sizes, each having substantially the same dimensions except for the length of the tube itself, may be used with a majority of patients. The smaller size desirably has a tube length extending between the opposed surfaces of the semi-spherical portion 4 and wing 24, 25 at opposite ends of the tube of approximately 0.590 inch for use with small patients, the intermediate size desirably has a tube length of approximately 1.1 inch for use with medium size patients, and the larger size desirably has a tube length of approximately 1.7 inch for larger patients.

Typically the oter dimensions of the device are desirably substantially as follows. The outer diameter (O.D.) of the tube 2 is desirably 0.362 inch, with the passage 7 therethrough having an inner diameter (I.D.) of approximately 0.250 inch, thus leaving a wall thickness of approximately 0.112 inch. The wall thickness of the mushroom shaped tip 3 is also desirably substantially the same as that of the tube, and such tip has a maximum O.D. of approximately 0.850 inch.

For other uses, the tube length may vary within a range of 0.5 to 2.0 inches. Also, the other dimensions may vary as well. For example, for an illeostomy, the O.D. of the tube may have to be greater. Also, the maximum O.D. of the mushroom shaped tip can be within a range of 0.6 to 1.5 inches.

The flapper valve 15 may have a thickness of approximately 0.040 inch and a groove 21 depth of approximately 0.020 inch, with an included angle between the opposite sides of the groove of approximately 120°. Also, the flapper valve may have an overall length of approximately 0.440 inch and a overall width of approximately 0.350 inch. Both ends of the flapper valve are desirably radiused to correspond in shape to the internal end wall 16 of the semi-cylindrical portion 4. Also, the end 28 of the flapper valve 15 remote from the flanged projections 18 is desirably tapered at an angle of approximately 45° over approximately 0.028 inch of its thickness from the side 20 toward the side 17. The flanged projections 18 on the flapper valve 15 are desirably spaced apart approximately 0.238 inch.

The integrally molded wings 24, 25 at the axial outer end of the tube have a wall thickness of approximately 0.125 inch, a width of approximately 0.400 inch, and a combined length of approximately 1.25 inch. One of the wings 25 has a rounded outer end, whereas the outer end of the other wing 24 is desirably substantially straight across, with the flexible membrane 27 being integrally molded thereto, such membrane being approximately 0.020 inch thick, 0.400 inch wide, and 0.830 inch long, and extending from the inner face of the wing 24 for connection of the plug 26 thereto. The axial outer edge of the radial outer end of the wing 24 is desirably rounded to facilitate wrapping of the flexible membrane 27 around the wing 24 when the plug 26 is inserted into the outer open end of the passage 7 during periods of non-use to close off the passage. For feedings or administration of medication, the plug 26 is removed from the tube and a simple hollow adaptor (not shown) may be inserted through the passage 7 from the outer end thereof to move the flapper valve 15 to the open position shown in FIG. 7. The adaptor may be connected to another tube leading to a feeding source or the like. After feeding has been completed, the tube 2 is flushed with water, the adaptor is removed, and the plug 26 is reinserted into the outer end of the passage 7.

From the foregoing, it will be apparent that the device of the present invention is easily inserted and self-retaining, with the outer end of the device remaining substantially flush with the skin. Because of the device's low profile, the device is not noticeable beneath the clothes of a patient and is not painful to wear. Also, there is little risk of dislodgement of the device, and the device is easy to use. Furthermore, the material of the device is minimally irritating to the skin, and if irritation should start to occur due to other causes, the device can easily be rotated a part turn to cause the retention wings to engage another portion of the skin that was previously exposed. Moreover, the device can be inserted into other viscera of the body for other applications as well, including, for example, urinary bladder drainage, ileostomy, jejunostomy, and cystostomy.

Although the invention has been shown and described with respect to a certain preferred embodiment, it is obvious that equivalent alterations and modifications will occur to others skilled in the art upon the reading and understanding of the specification. The present invention includes all such equivalent alterations and modifications, and is limited only by the scope of the claims.

We claim:

1. A device designed to be inserted through an opening in the wall of the abdomen and stomach or other viscera of a patient comprising a hollow tube member having an inner end and an outer end, and a longitudinal passage extending completely through said tube member from one end to the other, an enlarged resiliently deformable tip at the inner end of said tube member, said enlarged tip being hollow and having an end wall surrounding the inner end of said tube member, flapper valve means mounted interiorly of said enlarged tip, said flapper valve means having one end mounted on said end wall radially outwardly of said passage, said flapper valve means overlying the inner end of said passage for direct sealing engagement therewith for preventing reflux of fluids into said tube member from said enlarged tip while permitting the influx of fluids through said tube member and past said flapper valve means into said enlarged tip, and opening means in said enlarged tip permitting the passage of fluid entering said tip from said tube member through said flapper valve means.

2. The device of claim 1 wherein said flapper valve means has a pair of flanged projections extending from one side adjacent one end thereof radially outwardly of said inner end of said tube member, and said end wall has correspondingly shaped openings therein for receipt of said flanged projections for attaching said flapper valve means to said end wall.

3. The device of claim 2 further comprising adhesive means between said one end of said flapper valve means and said end wall of said tip radially outwardly of said inner end of said tube member to aid in mounting said flapper valve means to said end wall.

4. The device of claim 1 wherein said end wall is relatively flat around said inner end of said tube, and said flapper valve means is relatively flat on one side for flat sealing engagement with said end wall around said inner end of said tube.

5. The device of claim 4 wherein the other side of said flapper valve means has a substantially V-shaped groove therein extending substantially the full width of said flapper valve means adjacent the inner diameter of said tube passage at the inner end thereof to provide a bend line about which the other end of said flapper valve means is free to flex for opening and closing the inner end of said passage.

6. The device of claim 5 wherein said other side of said flapper valve means is substantially flat except for said V-shaped groove.

7. The device of claim 1 wherein said device is made of a resiliently deformable plastic-like material, and said tip includes an enlarged semi-spherical portion integrally molded on the inner end of said tube member, said semi-spherical portion including said end wall on which said flapper valve means is mounted, and a separately molded outer cap portion which is adhesively secured to said semi-spherical portion after the mounting of said flapper valve means to said end wall, said outer cap portion having said opening means therein.

8. The device of claim 7 wherein the end of said semi-spherical portion remote from said end wall has a counterbore therein, and said outer cap portion has a stepped shoulder thereon for receipt in said counterbore to provide overlapping surfaces therebetween which are bonded together by an adhesive.

9. The device of claim 7 further comprising flange means integrally molded on the outer end of said tube member, the axial distance between the opposed surfaces of said tip and flange means substantially corresponding to the distance between the inside wall of the stomach and the outer abdominal wall of a patient, whereby when said device is inserted through an opening in the abdomen and stomach and the tip has expanded against the inside wall of the stomach, said flange means rests generally flush with the outside abdominal wall to make said device self-retaining.

10. The device of claim 9 wherein said tube member has a length between said opposed surfaces of approximately 0.5 to 2.0 inches.

11. The device of claim 9 wherein said tube member has a length between said opposed surfaces of approximately 0.590 inches for smaller patients, approximately 1.1 inch for intermediate size patients, and approximately 1.7 inch for larger patients.

12. The device of claim 9 wherein said flange means comprises a pair of diameterically spaced, oppositely extending, substantially flat wings integrally molded on the outer end of said tube member.

13. the device of claim 12 wherein said wings are relatively narrow in width whereby if irritation of the skin should occur in the area of said wings, said tube member can be rotated a part turn to cause said wings to overlie a different non-irritated area of the skin.

14. The device of claim 13 wherein said wings have a width of approximately 0.400 inch.

15. The device of claim 14 further comprising a plug integrally connected to the radial outer end of one of said wings by a flexible membrane which permits said plug to be inserted into the outer open end of said passage to completely close off said passage at the outer end of said tube member and removed therefrom as desired.

16. A device designed to be inserted through an opening into the stomach or other viscera of a patient comprising a hollow tube member made of a resiliently deformable plastic-like material, said hollow tube member having inner and outer ends and a longitudinal passage extending through said tube member from one end to the other, an enlarged resiliently deformable tip at the inner end of said tube member, said enlarged tip being hollow and having a relatively flat, radially extending end wall surrounding the inner end of said tube member, resiliently deformable flapper valve means having one end mounted on said end wall radially outwardly of the open inner end of said passage, said flapper valve means extending over the open inner end of said passage in sealing engagement with said end wall for preventing reflux of fluids into said passage from said enlarged tip while permitting the influx of fluids through said passage into said enlarged tip, and opening means in said enlarged tip for the passage of fluids entering said enlarged tip through said flapper valve means from said tube member, said enlarged tip including an enlarged semi-spherical portion integrally molded on the inner end of said tube member, said semi-spherical portion including said end wall onto which said flapper valve mens is mounted, and a separately molded outer cap portion which is adhesively secured to said semi-spherical portion after the mounting of said flapper valve means to said end wall of said semi-spherical portion, said outer cap portion having said opening means therein, a pair of diametrically spaced, oppositely extending, substantially flat wings integrally molded to the outer end of said tube member, the relative spacing between the opposed surfaces of said enlarged tip and wings substantially corresponding to the distance between the inside wall of the stomach and outside abdominal wall of a patient whereby when the device is inserted through an opening in the abdomen and stomach and the enlaged tip has expanded against the inside wall of the stomach, said wings rest generally flush with the outside abdominal wall to make said device self-retaining, said wings being relatively narrow in width whereby if irritation of the skin should occur in the area of said wings, said tube member can be rotated a part turn to cause said wings to overlie a different non-irritated area of the skin, and a plug integrally connected to one of said wings by a flexible membrane which permits said plug to be inserted into the outer open end of said passage to completely close off said passage at the outer end of said tube member and removed therefrom as desired.

17. The device of claim 16 wherein said flapper valve means has a pair of flanged projections extending from one side adjacent one end thereof, and said end wall has correspondingly shaped openings therein radially outwardly of said inner end of said tube for receipt of said flanged projections for mounting of said flapper valve means to said end wall, said flapper valve means being relatively flat on said one side for sealing engagement with said end wall, and the other side of said flapper valve means having a substantially V-shaped groove therein exending substantially the full width of said flapper valve means substantially in line with the inner diameter of said passage at the open inner end of said tube member to provide a bend line about which the other end of said flapper valve means is free to flex for openng and closing of said passage at said inner end of said tube member, said other side of said flapper valve means being substantially flat except for said V-shaped groove.

18. A device designed to be inserted through an opening in the wall of the abdomen and stomach or other viscera of a patient comprising a hollow tube member having an inner end and an outer end, and a longitudinal passage extending completely through said tube member from one end to the other, an enlarged resiliently deformable tip at the inner end of said tube member, valve means within said device for preventing reflux of fluids through said tube member from said enlarged tip while permitting the influx of fluids through said tube member into said enlarged tip, opening means in said enlarged tip permitting the passage of fluid entering said tip from said tube member through said valve means, a pair of diametrically spaced, oppositely, extending, substantially flat wings integrally molded on the outer end of said tube member, the axial distance between the opposed surfaces of said tip and said wings substantially corresponding to the distance between the inside wall of the stomach and the outer abdominal wall of a patient, whereby when said device is inserted through an opening in the abdomen and stomach and the tip has expanded against the inside wall of the stomach, said wings rest generally flush with the outside abdominal wall to make said device self-retaining, said wings being relatively narrow in width whereby if irritation of the skin should occur in the area of said wings, said tube member can be rotated a part turn to cause said wings to overlie a different non-irritated area of the skin.

19. The device of claim 18 further comprising a plug integrally connected to the radial outer end of one of said wings by a flexible membrane which permits said plug to be inserted into the outer open end of said passage to completely close off said passage at the outer end of said tube member and removed therefrom as desired.

20. The device of claim 18 wherein said enlrged tip has an end wall surrounding the inner end of said tube member, and said valve means comprises a valve member having one end mounted on said end wall radially outwardly of said passage, said valve means overlying the inner end of said passage for preventing reflux of fluids into said tube member from said enlarged tip while permitting the influx of fluids through said tube member and past said valve means into said enlarged tip.

21. A device designed to be inserted through an opening in the wall of the abdomen and stomach or other viscera of a patient comprising a hollow tube member having an inner end and an outer end, and a longitudinal passage extending completely through said tube member from one end to the other, an enlarged resiliently deformable tip at the inner end of said tube member, valve means within said device for preventing reflux of fluids through said tube member from said enlarged tip while permitting the inflx of fluids through said tube member into said enlarged tip, opening means in said enlarged tip permitting the passage of fluid entering said tip from said tube member through said valve means, a pair of diametrically spaced, oppositely extending, substantially flat wings integrally molded on the outer end of said tube member, the axial distance between the opposed surfaces of said tip and said wings substantially corresponding to the distance between the inside and outside walls of the viscera of a patient, whereby when said device is inserted through an opening in the viscera and the tip has expanded against the inside wall of the viscera, said wings rest generally flush with the outside wall to make said device self-retaining, said wings being relatively narrow in width whereby if irritation of the skin should occur in the area of said wings, said tube member can be rotated a part turn to cause said wings to overlie a different non-irritated area of the skin.

22. The device of claim 21 wherein said device is made of a resiliently deformable plastic-like material, and said tip includes an enlarged portion integrally molded on the inner end of said tube member.

23. The device of claim 22 wherein said enlarged portion is generally semi-spherical and has a separately molded outer cap portion adhesively secured thereto, said outer cap portion having said opening means therein.

24. The device of claim 23 wherein said enlarged portion has a counterbore therein, and said outer cap portion has a stepped shoulder therein for receipt in said counterbore to provide overlapping surfaces therebetween which are bonded together by an adhesive.

* * * * *

REEXAMINATION CERTIFICATE (1634th)
United States Patent [19]
Gauderer et al.

[11] B1 4,863,438
[45] Certificate Issued  Jan. 28, 1992

[54] LOW PROFILE GASTROSTOMY DEVICE

[75] Inventors: Michael L. Gauderer, Cleveland; George J. Picha, Independence; Dennis Siedlak, Willoughby Hills, all of Ohio

[73] Assignee: Applied Medical Tech., Inc.

Reexamination Request:
No. 90/002,145, Sep. 21, 1990

Reexamination Certificate for:
Patent No.: 4,863,438
Issued: Sep. 5, 1989
Appl. No.: 803,386
Filed: Nov. 29, 1985

[51] Int. Cl.$^5$ ............................................. A61M 5/005
[52] U.S. Cl. .................................. 604/247; 604/105; 604/175; 604/256
[58] Field of Search ................. 604/93, 101, 117, 279, 604/104, 175, 297, 105, 96, 178, 271, 280, 247, 256

[56] References Cited
U.S. PATENT DOCUMENTS

| | | |
|---|---|---|
| 3,788,327 | 1/1974 | Donowitz et al. |
| 3,856,021 | 12/1974 | McIntosh |
| 3,871,380 | 3/1975 | Heros |
| 4,311,148 | 1/1982 | Courtney et al. |
| 4,315,513 | 2/1982 | Nawash et al. |
| 3,915,171 | 10/1975 | Shermeta |

OTHER PUBLICATIONS

A 1939 article by Dr. Glassman entitled "A New Aseptic Double-Valved Tubogastrostomy" (1939 Glassman article).
Article appearing in Surgery, Gynecology & Obstetrics, Oct. 1956, at pp. 517-520 (Oct. 1956 SGO article).
Article appearing in Surgery, vol. 61, No. 2, Feb., 1967, at pp. 320-324 (Feb. 1967 Surgery article).
Article appearing in The American Journal of Surgery, vol. 141, Mar. 1981 at pp. 391-392 (Mar. 1981 AJS article).
Abstract distributed at an American Pediatric Surgical Association meeting on or about May 9 through 12, 1984 entitled "The Gastrostomy Button—A Simple, Skin Level, Non-refluxing Device for Long-term Internal Feedings" (May 1984 Abstract).
Article appearing in Journal of Pediatric Surgery, Volume 15, No. 6, December, 1980, at pages 872-875 (1980 JPS article).
Article Appearing in American Society for Gastrointestinal Endoscopy, Volume 27, No. 1, 1981, at pages 9-11 (1981 ASGE article).
August 1984 Mentor brochure.

*Primary Examiner*—C. Fred Rosenbaum

[57] ABSTRACT

Device includes a flexible, hollow tube portion having a resiliently deformable mushroom shape tip at the inner end thereof to retain the tube in the stomach or other viscera of a patient and provide an enlarged internal chamber for the mounting of a one-way flapper valve therein and the seating of the flapper valve against the inner end of the tube portion to prevent reflux of gastric contents while permitting the influx of fluids into the stomach or other viscera of the patient through the tube portion. A pair of oppositely extending, relatively short, flat wings are integrally molded on the outer end of the tube portion to make the tube portion self-retaining and flush up against the skin. The wings are relatively narrow in width, whereby the tube portion may be rotated a part turn to bring the wings into contact with different areas of the skin if irritation should occur. A plug is integrally molded on the outer end of one of the wings by a flexible membrane which permits the plug to be inserted into the tube at the outer end thereof and removed therefrom as desired.

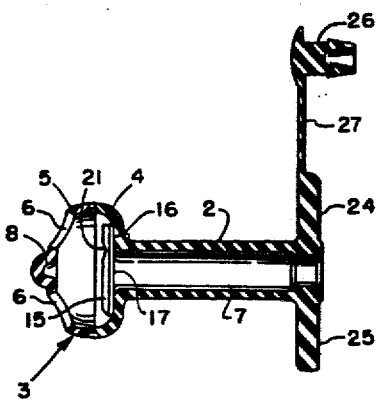

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-24 is confirmed.

* * * * *